(12) United States Patent
Spataro

(10) Patent No.: US 11,771,882 B2
(45) Date of Patent: Oct. 3, 2023

(54) CATHETER ADAPTERS

(71) Applicant: Becton, Dickinson and Company, Franklin Lakes, NJ (US)

(72) Inventor: Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 166 days.

(21) Appl. No.: 16/993,062

(22) Filed: Aug. 13, 2020

(65) Prior Publication Data

US 2021/0052879 A1 Feb. 25, 2021

Related U.S. Application Data

(60) Provisional application No. 62/889,375, filed on Aug. 20, 2019.

(51) Int. Cl.
*A61M 25/06* (2006.01)
*A61M 39/10* (2006.01)

(52) U.S. Cl.
CPC ......... *A61M 39/10* (2013.01); *A61M 25/0606* (2013.01); *A61M 2039/1077* (2013.01)

(58) Field of Classification Search
CPC .............. A61M 25/0097; A61M 25/02; A61M 25/0606; A61M 2025/028
See application file for complete search history.

(56) References Cited

U.S. PATENT DOCUMENTS

| | | | | |
|---|---|---|---|---|
| 5,456,671 | A | * 10/1995 | Bierman | A61M 5/158 604/174 |
| 2011/0202123 | A1 | * 8/2011 | Bonutti | A61M 25/065 604/27 |
| 2013/0178798 | A1 | * 7/2013 | Pearson | A61M 25/0612 604/164.08 |
| 2014/0221932 | A1 | * 8/2014 | Puhasmagi | A61M 25/0606 604/167.05 |
| 2016/0015932 | A1 | * 1/2016 | Catudal | A61M 25/0097 604/164.01 |
| 2017/0239443 | A1 | * 8/2017 | Abitabilo | A61M 39/28 |
| 2018/0318557 | A1 | 11/2018 | Burkholz et al. | |
| 2019/0151567 | A1 | * 5/2019 | Cote | A61M 5/3287 |

FOREIGN PATENT DOCUMENTS

| | | |
|---|---|---|
| WO | 2014/134248 | 9/2014 |
| WO | 2017/042359 | 3/2017 |
| WO | 2017/074673 | 5/2017 |
| WO | 2017/143176 | 8/2017 |

* cited by examiner

*Primary Examiner* — Amber R Stiles
*Assistant Examiner* — Leah J Swanson
(74) *Attorney, Agent, or Firm* — KIRTON MCCONKIE; Whitney Blair; Kevin Stinger

(57) ABSTRACT

A catheter adapter may include a catheter adapter body and a catheter adapter channel formed within the catheter adapter body. The catheter adapter body may include a proximal end, a distal end, an inferior surface, and a superior surface. The inferior surface of the catheter adapter body may be configured to abut against a surface area of a patient's skin, and an angle formed between the surface area of the patient's skin and a longitudinal axis of the catheter adapter channel may be greater than 4 degrees.

7 Claims, 12 Drawing Sheets

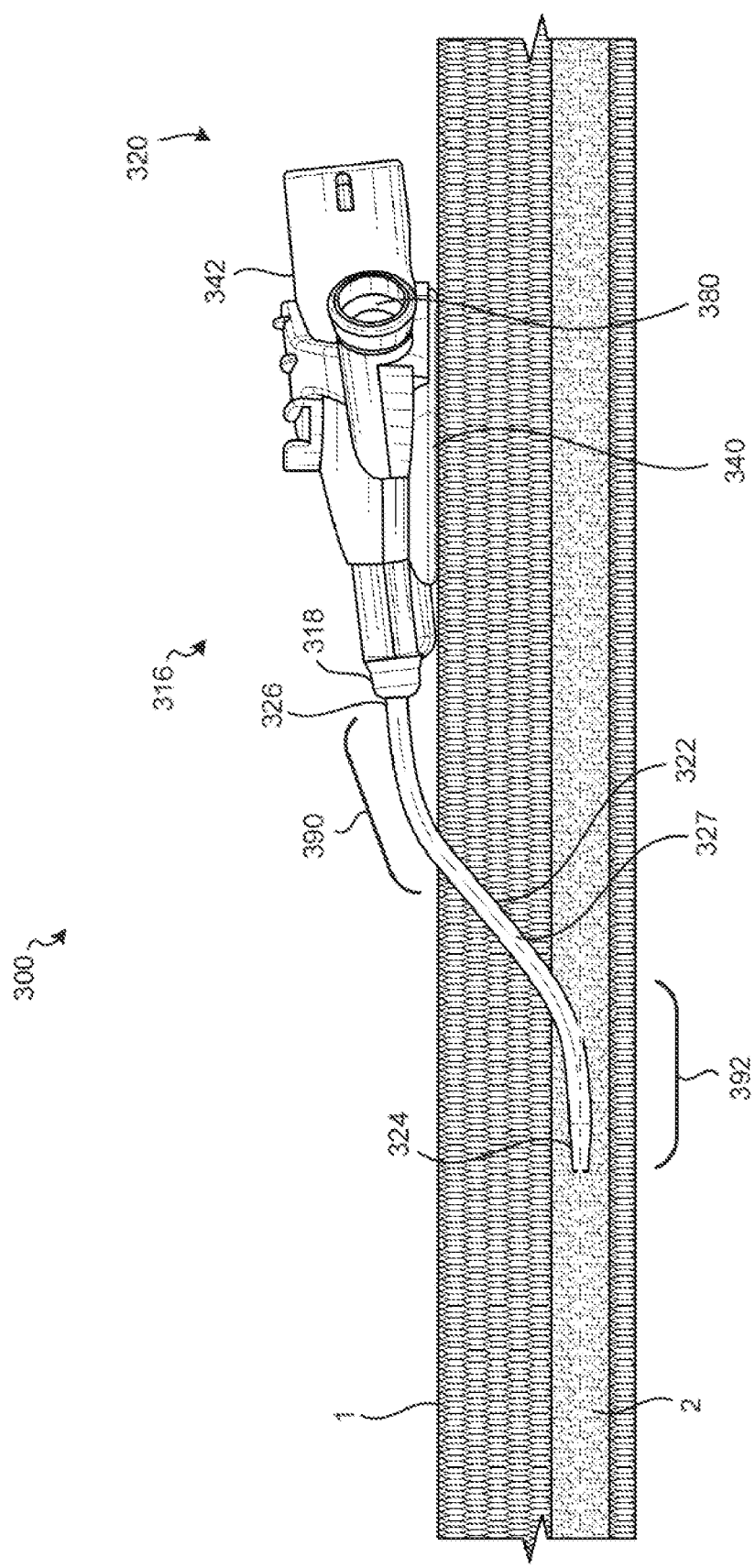

CATHETER ADAPTERS

RELATED APPLICATIONS

This application claims the benefit of U.S. Provisional Application No. 62/889,375, filed Aug. 20, 2019, and entitled CATHETER ADAPTERS which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are typically inserted at a shallow angle through the skin and into a blood vessel of the patient, such as an artery, a vein, or any other vasculature of the patient.

In order to verify proper placement of the introducer needle and/or the PIVC within a blood vessel, a clinician will typically watch for blood "flashback" to occur within the PIVC. Blood flashback occurs when blood travels proximally between an outer surface of the introducer needle and an inner surface of the PIVC, which may be transparent. Thus, the clinician may visualize the blood and confirm placement of the introducer needle within the blood vessel. Once placement of the needle has been confirmed, the clinician may temporarily occlude flow in the vein, remove the introducer needle, and secure the PIVC to the patient's skin with dressing to keep the PIVC in place for future blood withdrawal and/or fluid infusion.

However, traditional catheter adapter designs can have characteristics that may increase the likelihood of complications including, but not limited to: (1) a reduced "in-vein" length for a given catheter lumen; (2) dislodgement of the catheter lumen from the vein; (3) infiltration and/or extravasation of medication/fluid into surrounding tissues; (4) phlebitis; (5) occlusion of the catheter lumen (e.g., the tip of the catheter lumen may become stuck in a vein wall and become occluded); (6) increased stress forces experienced by the catheter lumen and the vein; (7) a larger "un-productive" length of the catheter lumen that couples an increased volume of fluid; and (8) a larger catheter adapter foot print that can lead to compromising loading scenarios on the catheter lumen when the catheter adapter is secured to the patient's skin with dressing.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related systems.

In some embodiments, a catheter assembly may include a catheter adapter body and a catheter. The catheter adapter body may include a proximal end, a distal end, an inferior surface, a superior surface, and a catheter adapter channel formed within the catheter adapter body. The catheter may include a proximal end, a distal end, and a catheter lumen extending between the proximal and distal ends of the catheter. The proximal end of the catheter may be coupled to the catheter adapter body such that the catheter lumen is in fluid communication with the catheter adapter channel, and an angle formed between the inferior surface of the catheter adapter body and a first longitudinal axis of the catheter adapter channel may be greater than 4 degrees.

In some embodiments, the catheter adapter body of the catheter assembly may include a second longitudinal axis extending between the proximal and distal ends of the catheter adapter body, and an angle formed between the first and second longitudinal axes may be greater than 10 degrees.

In some embodiments, the angle formed between the first and second longitudinal axes may be between 10 degrees and 90 degrees.

In some embodiments, the angle formed between the first and second longitudinal axes may be 30 degrees.

In some embodiments, at least a portion of the catheter lumen proximate the catheter adapter body may be coaxial with the catheter adapter channel formed within the catheter adapter body.

In some embodiments, the catheter assembly may include a septum coupled to the catheter adapter body adjacent the catheter adapter channel. In some embodiments, the septum may be a single component septum. In some embodiments, the septum may be a multi-component septum.

In some embodiments, the catheter adapter body may include an access port in fluid communication with the catheter adapter channel.

In some embodiments, a catheter adapter may include a catheter adapter body and a catheter adapter channel. The catheter adapter body may include a proximal end, a distal end, an inferior surface, and a superior surface. The catheter adapter channel may be formed within the catheter adapter body. The inferior surface of the catheter adapter body may be configured to about a surface area of a patient's skin, and an angle formed between the surface area of the patient's skin and a longitudinal axis of the catheter adapter channel may be greater than 4 degrees.

In some embodiments, the angle formed between the surface area of the patient's skin and the longitudinal axis of the catheter adapter channel may be greater than 10 degrees.

In some embodiments, the angle formed between the surface area of the patient's skin and the longitudinal axis of the catheter adapter channel may be between 10 degrees and 90 degrees.

In some embodiments, the angle formed between the surface area of the patient's skin and the longitudinal axis of the catheter adapter channel may be 30 degrees.

In some embodiments, the catheter adapter may include a septum coupled to the catheter adapter body adjacent the catheter adapter channel.

In some embodiments, the septum may be a single component septum. In some embodiments, the septum may be a multi-component septum.

In some embodiments, the catheter adapter body may include an access port in fluid communication with the catheter adapter channel.

In some embodiments, a catheter system may include a catheter adapter, a catheter coupled to the catheter adapter, and a needle assembly. The catheter adapter may include a proximal end, a distal end, an inferior surface, a superior surface, and a catheter adapter channel formed within the catheter adapter. The catheter adapter may include a first longitudinal axis extending between the proximal and distal ends of the catheter adapter, such that the first longitudinal axis is substantially parallel to the inferior surface of the catheter adapter. The catheter may include a proximal end, a distal end, and a catheter lumen extending between the proximal and distal ends of the catheter. The proximal end of the catheter may be coupled to the catheter adapter such that the catheter lumen is in fluid communication with the catheter adapter channel, and an angle formed between the first longitudinal axis of the catheter adapter and a second longitudinal axis of the catheter may be greater than 4 degrees. The needle assembly may include a needle hub and an introducer needle coupled to the needle hub. The introducer needle may be configured to be removably insertable within the catheter adapter channel and the catheter lumen.

In some embodiments, the angle formed between the first longitudinal axis of the catheter adapter and the second longitudinal axis of the catheter may be greater than 10 degrees.

In some embodiments, the angle formed between the first longitudinal axis of the catheter adapter and the second longitudinal axis of the catheter may be between 10 degrees and 90 degrees.

In some embodiments, the angle formed between the first longitudinal axis of the catheter adapter and the second longitudinal axis of the catheter may be 30 degrees.

In some embodiments, at least a portion of the catheter lumen proximate the catheter adapter may be coaxial with the catheter adapter channel formed within the catheter adapter.

In some embodiments, the catheter system may include a septum coupled to the catheter adapter adjacent the catheter adapter channel. In some embodiments, the septum may be a single component septum. In some embodiments, the septum may be a multi-component septum.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which:

FIG. 3A is a side view of an example catheter assembly 300 inserted into a blood vessel 2 of a patient, according to some embodiments;

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1A:
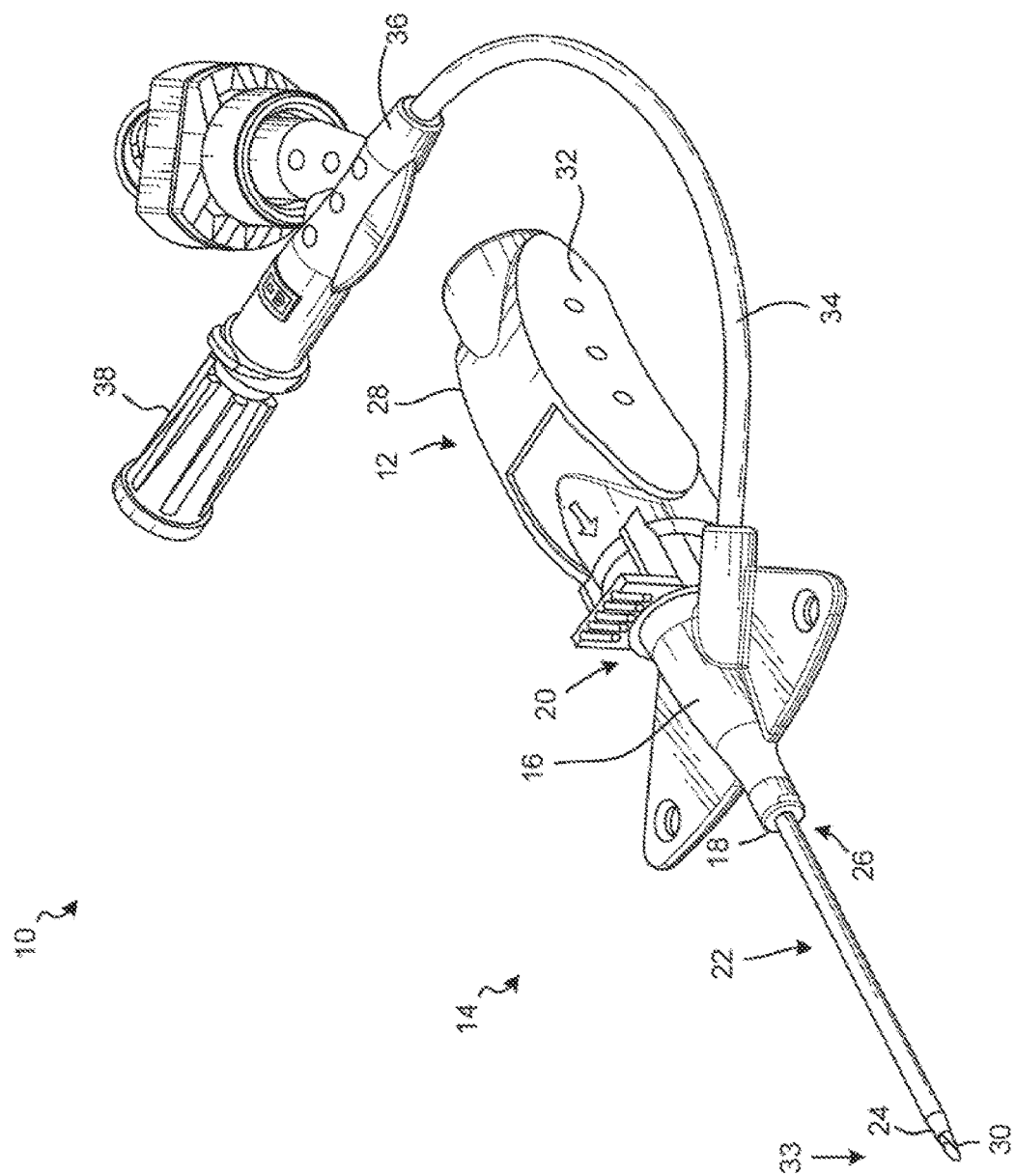
FIG. 1A is a perspective top view of an example catheter system 10, according to some embodiments.
Figure 1B:
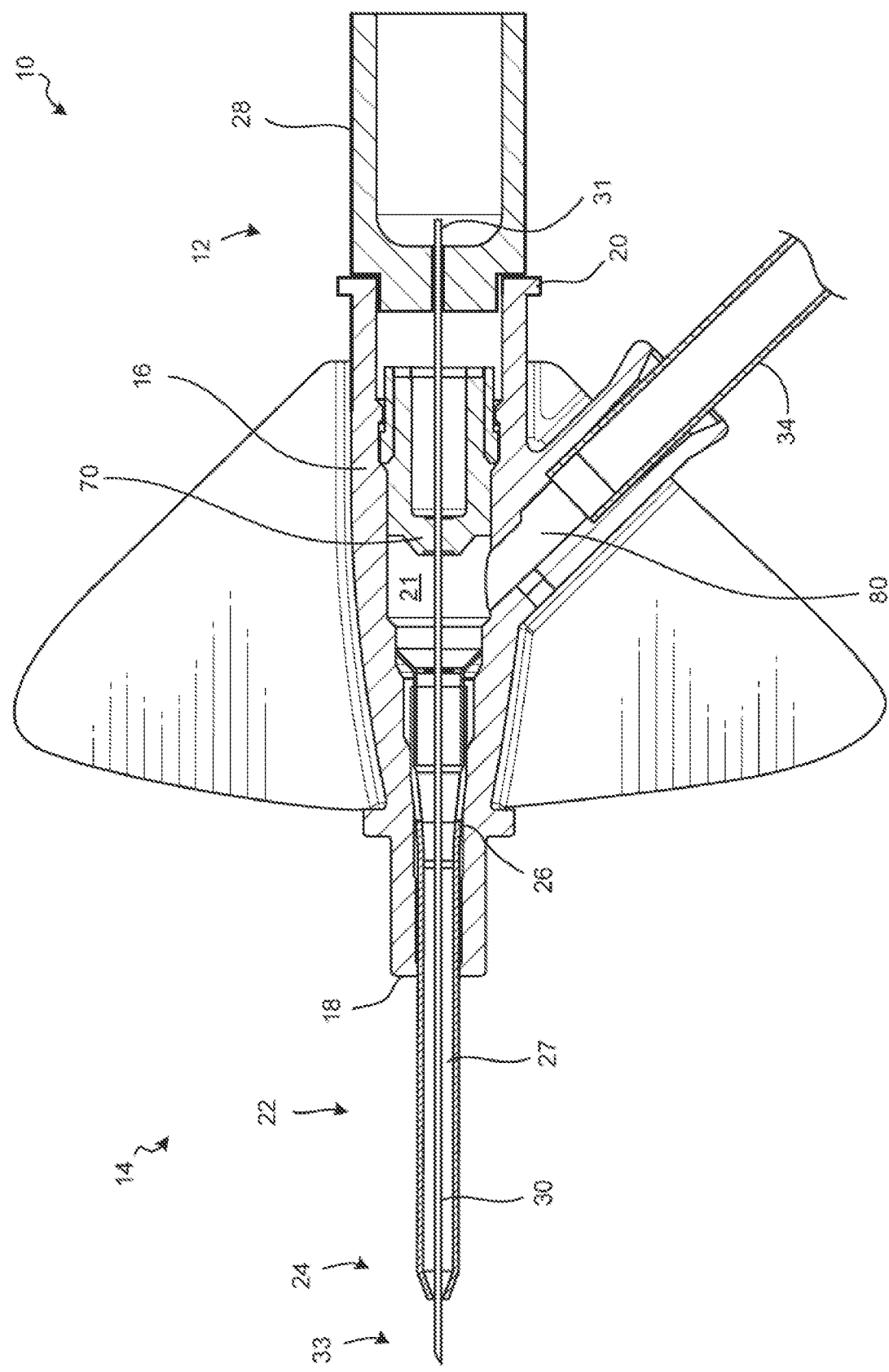
FIG. 1B is a cross-sectional top view of the catheter system 10 of FIG. 1A, according to some embodiments.

Referring to FIGS. 1A and 1B, in some embodiments, a catheter system 10 may include a needle assembly 12 and a catheter assembly 14, according to some embodiments. FIGS. 1A and 1B illustrate the catheter system 10 in an insertion position, ready for insertion into a vein of a patient (not shown in FIGS. 1A and 1B). In some embodiments, the catheter assembly 14 may include a catheter adapter or catheter adapter body 16, which may include a proximal end 20, a distal end 18, and a catheter adapter channel 21 formed with the catheter adapter body 16 and extending between the proximal and distal ends 20, 18 of the catheter adapter body 16. In some embodiments, the catheter adapter body 16 may include a septum 70 coupled to the catheter adapter body 16 adjacent the catheter adapter channel 21. In some embodiments, the septum 70 may be a single component septum. In some embodiments, the septum 70 may be a multi-component septum. In some embodiments, the catheter assembly 14 may include a catheter 22, which may include a proximal end 26, a distal end 24, and a catheter lumen 27 extending between the proximal and distal ends 26, 24 of the catheter 22. In some embodiments, the catheter 22 may include a peripheral intravenous catheter ("PIVC"). In some embodiments, the proximal end 26 of the catheter 22 may be secured within the catheter adapter body 16.

In some embodiments, the needle assembly 12 may include a needle hub 28, which may be removably coupled to the catheter adapter body 16. In some embodiments, the needle assembly 12 may include an introducer needle 30. In some embodiments, a proximal end 31 of the introducer needle 30 may be secured within the needle hub 28. In some embodiments, the introducer needle 30 may extend through the catheter lumen 27 and a distal end 33 of the introducer needle 30 may protrude from the distal end 24 of the catheter 22 when the catheter system 10 is in an insertion position and ready for insertion into a vein of a patient (not shown in FIGS. 1A and 1B).

In some embodiments, the needle assembly 12 may include a needle grip 32, which a clinician may grip and move proximally to withdraw the introducer needle 30 from the vein once placement of the catheter 22 within the vein is confirmed. In some embodiments, the catheter system 10 may include an extension tube 34. In some embodiments, a distal end of the extension tube 34 may be coupled to the catheter adapter body 16 and a proximal end of the extension tube 34 may be coupled to an adapter 36. In some embodiments, the catheter adapter body 16 may include an access port 80, which may be in fluid communication with the catheter adapter channel 21. In some embodiments, a distal end of the extension tube 34 may be coupled to the access port 80, such that the extension tube 34 may be in fluid communication with the catheter adapter channel 21 via the access port 80.

In some embodiments, a fluid infusion device (not shown) may be coupled to the adapter 36 to deliver fluid to the patient via the catheter 22 inserted in the vein, once the introducer needle 30 is removed from the catheter system 10. In some embodiments, a blood collection device (not shown) may be coupled to the adapter 36 to withdraw blood from the patient via the catheter 22 inserted in the vein.

The catheter system 10 may include straight, ported, integrated, and conventional catheters. For example, in some embodiments, the catheter system 10 may be integrated, having the extension tube 34 integrated within the catheter adapter body 16, such as, for example, the BD NEXIVA™ Closed IV Catheter System, the BD NEXIVA™ DIFFUSICS™ Closed IV Catheter System, the BD PEGASUS™ Safety Closed IV Catheter System, or another integrated catheter system. In some embodiments, the catheter system 10 may be non-integrated, without the extension tube 34.

In some embodiments, the catheter system 10 may be vented to observe blood and facilitate proximal flow of blood within the introducer needle 30 and/or the catheter 22. In some embodiments, the catheter system 10 may be vented in any suitable manner. For example, a vent plug 38 may be coupled to the adapter 36 during insertion of the catheter 22 into the patient. In some embodiments, the vent plug 38 may be permeable to air but not to blood. In some embodiments, the catheter 22, the catheter adapter body 16, the extension tube 34, the adapter 36, and the vent plug 38 may be in fluid communication. As another example, in some embodiments, the needle hub 28 may include a flash chamber.

Figure 2:
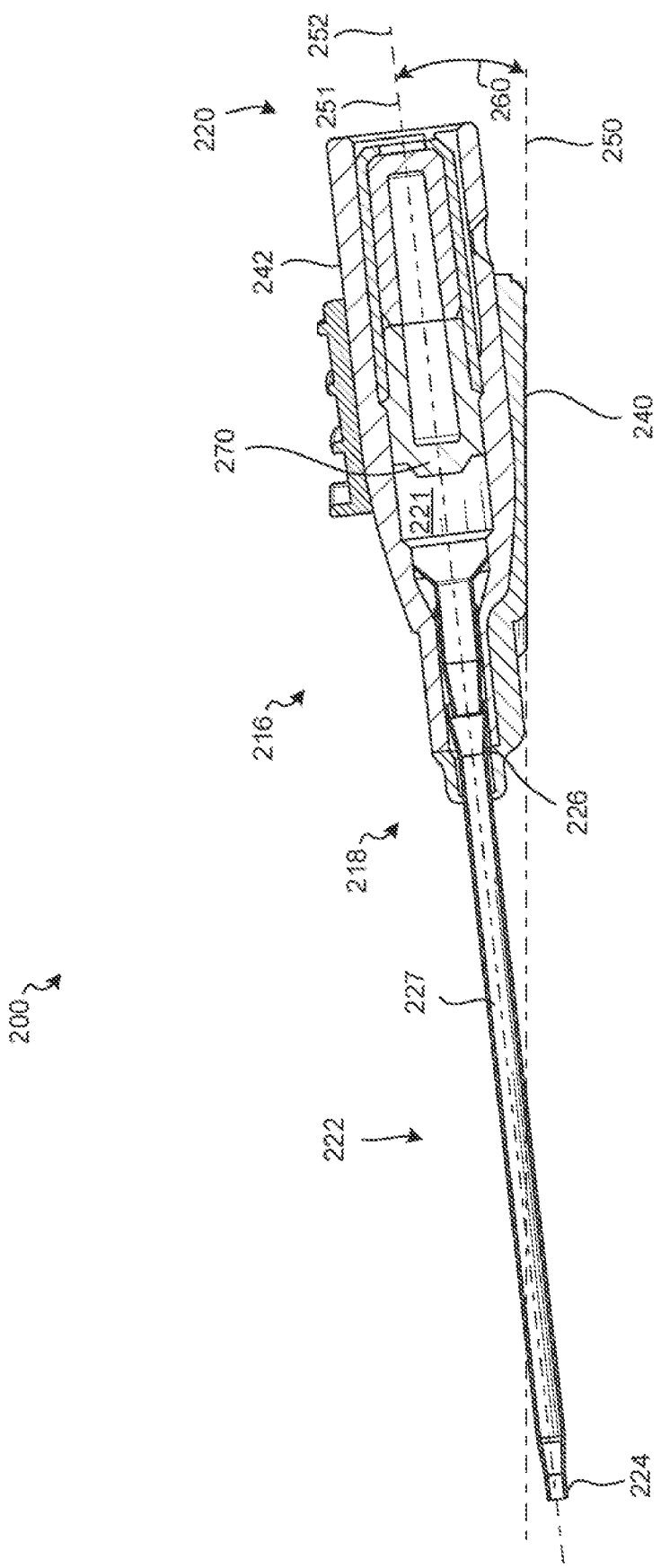
FIG. 2 is a cross-sectional side view of an example catheter assembly 200, according to some embodiments.

FIG. 2 illustrates a cross-sectional side view of an example catheter assembly 200, according to some embodiments. The catheter assembly 200 may generally include a catheter adapter body 216 and a catheter 222.

The catheter adapter body 216 may include a proximal end 220, a distal end 218, an inferior surface 240, a superior surface 242, and a catheter adapter channel 221 formed within the catheter adapter body 216 and extending between the proximal and distal ends 220, 218 of the catheter adapter body 216. In some embodiments, the catheter adapter body 216 may include a septum 270 which may be coupled to the catheter adapter body 216 adjacent the catheter adapter channel 221. In some embodiments, the septum 270 may be a single component septum. In some embodiments, the septum 270 may be a multi-component septum. In some embodiments, the catheter adapter body 216 may also include an access port (not shown in FIG. 2) that may be in fluid communication with the catheter adapter channel 221.

The catheter 222 may include a proximal end 226, a distal end 224, and a catheter lumen 227 extending between the proximal and distal ends 226, 224 of the catheter 222. In some embodiments, the catheter 222 may include a peripheral intravenous catheter ("PIVC"). In some embodiments, the proximal end 226 of the catheter 222 may be coupled to and/or secured within the catheter adapter body 216, such that the catheter lumen 227 may be in fluid communication with the catheter adapter channel 221 formed within the catheter adapter body 216.

In some embodiments, an angle 260 formed between the inferior surface 240 of the catheter adapter body 216 and a first longitudinal axis 251 of the catheter adapter channel 221 may be between 0 degrees and 4 degrees. The inferior surface 240 of the catheter adapter body 216 may be substantially parallel to the line 250 shown in FIG. 2. In the embodiment shown in FIG. 2, the first longitudinal axis 251 of the catheter adapter channel 221 may be equal to a second longitudinal axis 252 or primary axis of the catheter adapter body 216 which extends between the proximal and distal ends 220, 218 of the catheter adapter body 216. In this embodiment, the first longitudinal axis 251 of the catheter adapter channel 221 may be coaxial with the second longitudinal axis 252 of the catheter adapter body 216. Moreover, a longitudinal axis of the catheter lumen 227 may also be coaxial with the first and second longitudinal axes 251, 252, as can be seen in FIG. 2.

Figure 3B:
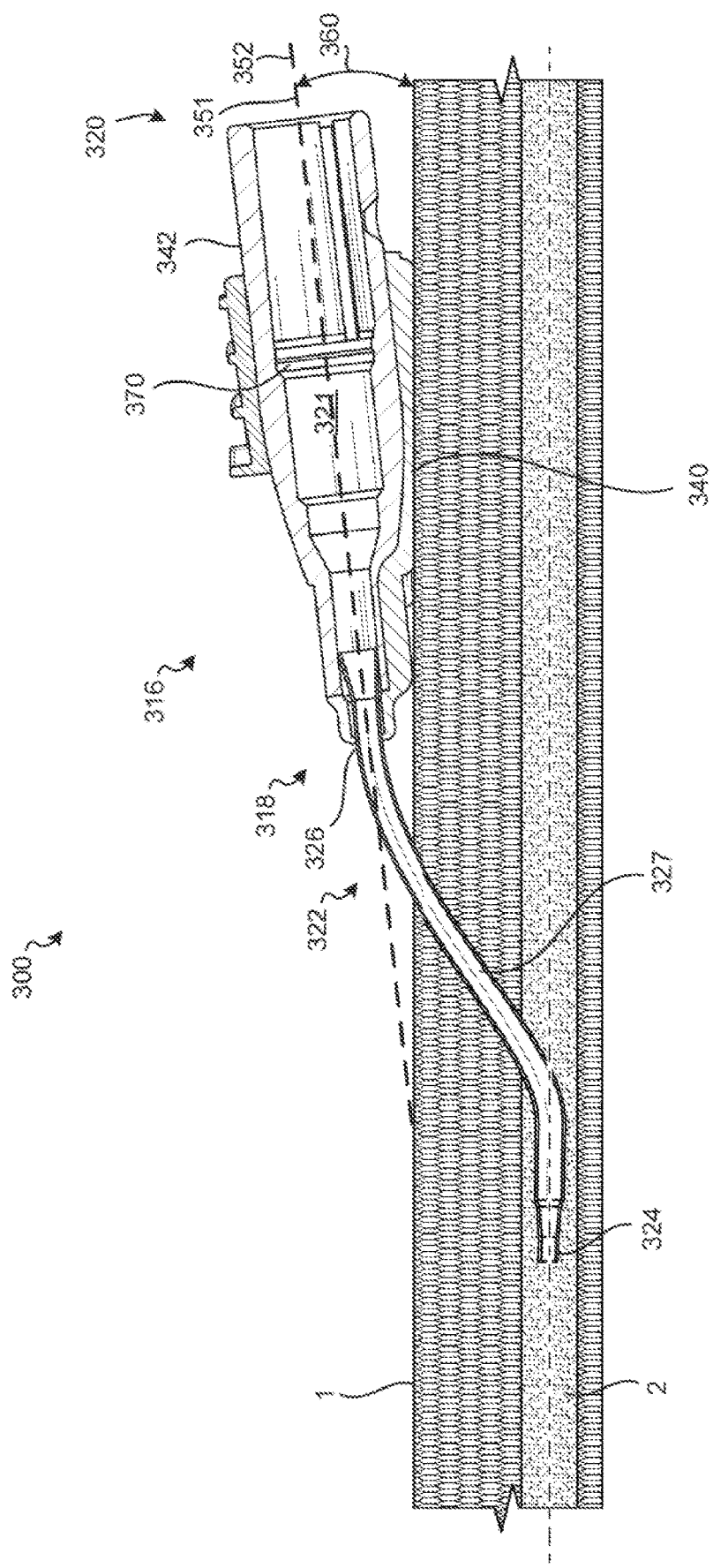
FIG. 3B is a cross-sectional side view of the catheter assembly 300 of FIG. 3A inserted into the blood 2 vessel of the patient, according to some embodiments.

FIGS. 3A and 3B illustrate a catheter assembly 300, similar to the catheter assembly 200 shown in FIG. 2. However, the catheter assembly 300 of FIGS. 3A and 3B is shown inserted into a blood vessel 2 of a patient with the inferior surface 340 of the catheter adapter body 316 abutting a surface area of the patient' skin 1. Specifically, FIG. 3A illustrates a side view of the catheter assembly 300, and FIG. 3B illustrates a cross-sectional side view of the catheter assembly 300 of FIG. 3A. The catheter assembly 300 may generally include a catheter adapter body 316 and a catheter 322.

The catheter adapter body 316 may include a proximal end 320, a distal end 318, an inferior surface 340, a superior surface 342, and a catheter adapter channel 321 formed within the catheter adapter body 316 and extending between the proximal and distal ends 320, 318 of the catheter adapter body 316. In some embodiments, the catheter adapter body 316 may include a septum 370 which may be coupled to the catheter adapter body 316 adjacent the catheter adapter channel 321. In some embodiments, the septum 370 may be a single component septum. In some embodiments, the septum 370 may be a multi-component septum. In some embodiments, the catheter adapter body 316 may also include an access port 380, which may be in fluid communication with the catheter adapter channel 321.

The catheter 322 may include a proximal end 326, a distal end 324, and a catheter lumen 327 extending between the proximal and distal ends 326, 324 of the catheter 322. In some embodiments, the catheter 322 may include a peripheral intravenous catheter ("PIVC"). In some embodiments, the proximal end 326 of the catheter 322 may be coupled to and/or secured within the catheter adapter body 316, such that the catheter lumen 327 may be in fluid communication with the catheter adapter channel 321 formed within the catheter adapter body 316.

In the embodiment shown in FIGS. 3A and 3B, the first longitudinal axis 351 of the catheter adapter channel 321 may be equal to a second longitudinal axis 352 of the catheter adapter body 316, which extends between the proximal and distal ends 320, 318 of the catheter adapter body 316 such that that the first longitudinal axis 351 of the catheter adapter channel 321 is coaxial with the second longitudinal axis 352 of the catheter adapter body 316, as shown in FIGS. 3A and 3B. Moreover, at least a portion of a longitudinal axis of the catheter lumen 327 proximate the distal end 318 of the catheter adapter body 316 may be coaxial with the first and second longitudinal axes 351, 352. In this manner, an angle formed between the longitudinal axis of the catheter adapter body 316 and the longitudinal axis of the catheter lumen 327 proximate the distal end 318 of the catheter adapter body 316 may be zero, due to these two axes being coaxial with each other, as shown in this embodiment.

In some embodiments, an angle 360 formed between the inferior surface 340 of the catheter adapter body 316 (and/or the surface area of the patient's skin abutting the inferior surface 340 of the catheter adapter body 316) and a first longitudinal axis 351 of the catheter adapter channel 321 may be between 0 degrees and about 4 degrees. The inferior surface 340 of the catheter adapter body 316 may be substantially parallel to the patient's skin 1 and/or substantially parallel to the surface area of the patient's skin abutting the inferior surface 340 of the catheter adapter body 316.

Accordingly, because the angle 360 shown in FIG. 3B is relatively small (e.g., between 0 degrees and 4 degrees), the catheter 322 may exhibit a substantial "S" shape bend in its profile because of this small angle 360, which may cause the distal end 318 of the catheter adapter body 316 to lift away from the patient's skin as the catheter adapter body 316 is secured to the patient's skin with dressing. This "S" shaped bend that is formed in the catheter 322 can reduce the effective in-vein length 392 of the catheter 322 toward the distal end 324 of the catheter 322, as can be seen in FIG. 3A.

In general, factors such as patient anatomy, insertion quality, and catheter adapter body design can impact the effective in-vein length of a given PIVC. As previously noted, smaller in-vein lengths are associated with complications such as dislodgements, phlebitis, anatomy-driven occlusions (e.g., the catheter tip is more likely to become stuck in a vein wall), etc.

The traditional design architecture of PIVC's places the primary axis of the catheter lumen substantially parallel to—and in many cases coincident with—the primary axis of the catheter adapter body, as is shown in FIGS. 2-3B. This traditional design architecture inherently limits the usable length of the catheter. Inserting the catheter near-parallel to the patient's skin causes the catheter to assume an "S" shape as it settles into position within the vein because the catheter traverses parallel to the patient's skin near the catheter adapter body before bending downward into the patient's tissue, and then bending in horizontally once more when the catheter enters into the vein. The upper portion of this "S" shape (e.g., see 390 in FIG. 3A) effectively reduces the in-vein length 392 of the catheter toward the distal end of the catheter, as shown in FIG. 3A. An improved catheter adapter design that reduces or eliminates this "S" shape bend in the catheter can effectively increase and/or maximize the in-vein length of a given PIVC.

Figure 4A:
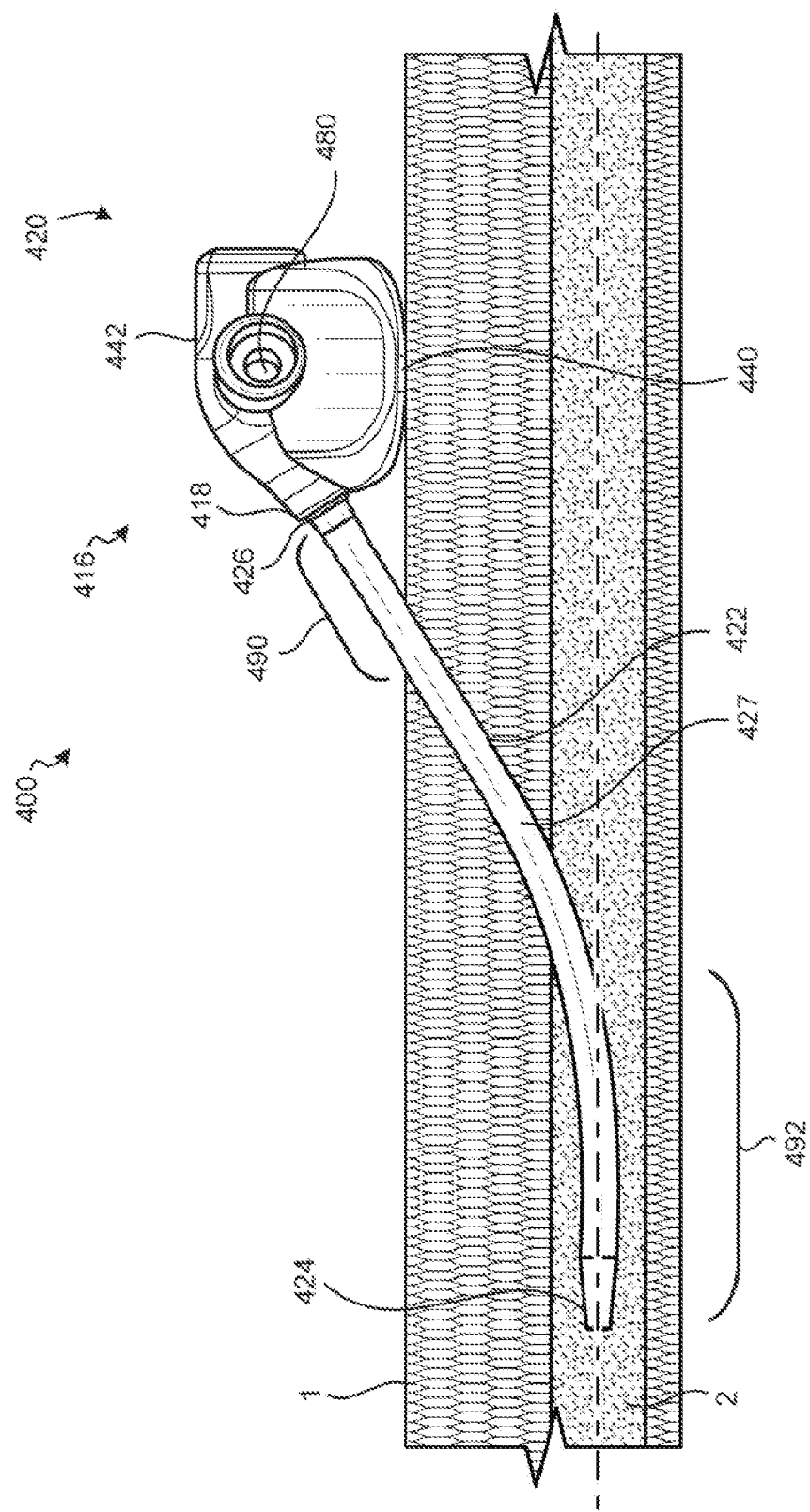
FIG. 4A is a side view of an example catheter assembly 400 inserted into the blood vessel 2 of the patient, according to some embodiments.
Figure 4B:
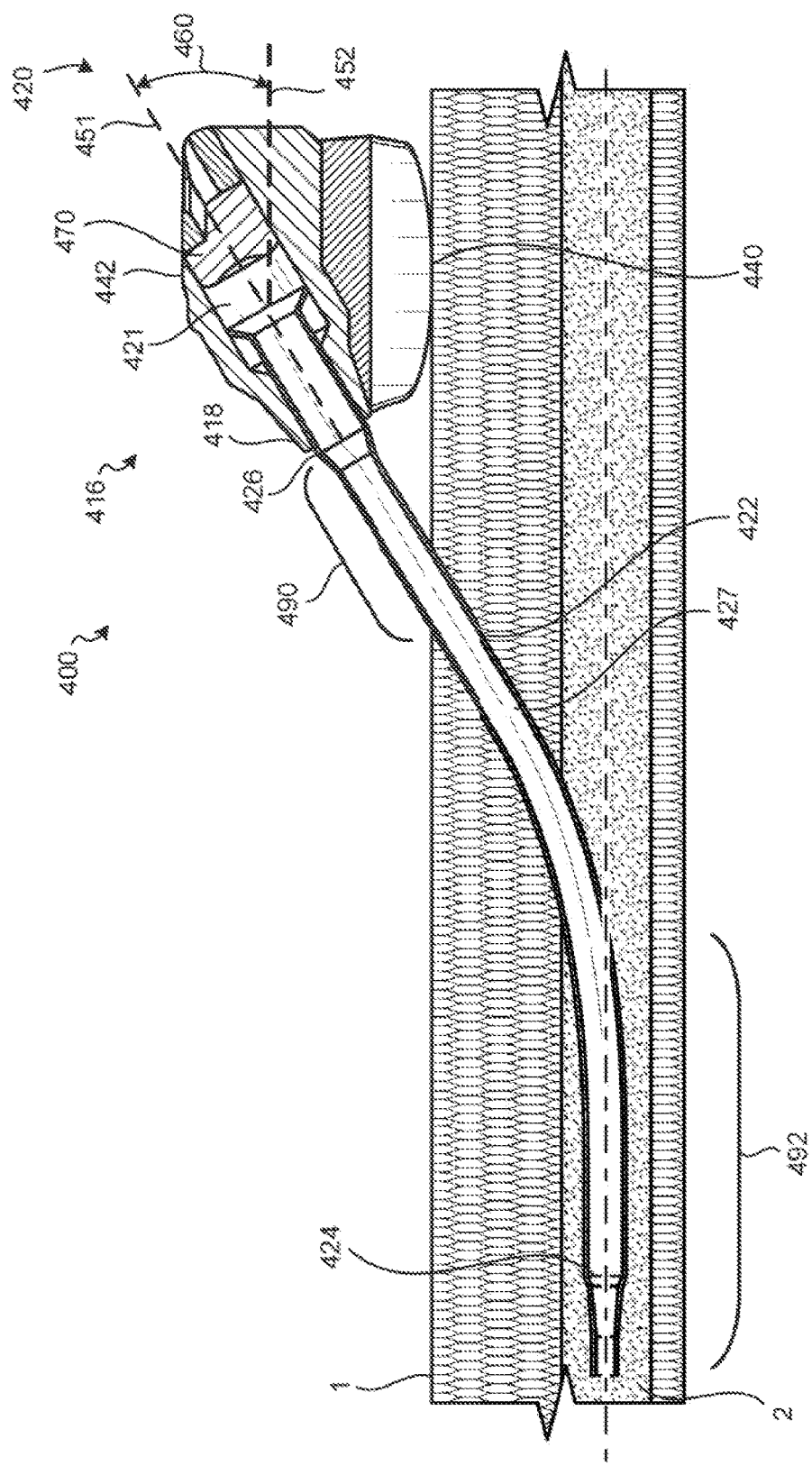
FIG. 4B is a cross-sectional side view of the catheter assembly 400 of FIG. 4A inserted into the blood vessel 2 of the patient, according to some embodiments.

FIGS. 4A and 4B illustrate an example catheter assembly 400 that reduces/eliminates the upper portion of an "S" shape bend formed in a catheter that is inserted into a blood vessel of a patient. Specifically, FIG. 4A illustrates a side view the catheter assembly 400 inserted into the blood vessel 2 of the patient and FIG. 4B illustrates a cross-sectional side view of the catheter assembly 400 of FIG. 4A inserted into the blood vessel 2 of the patient. Note how the upper portion 490 of the "S" shape has been reduced/eliminated, resulting in an increased in-vein length 492 toward the distal end 424 of the catheter 422.

The catheter assembly 400 may generally include a catheter adapter body 416 and a catheter 422. The catheter adapter body 416 may include a proximal end 420, a distal end 418, an inferior surface 440, a superior surface 442, and a catheter adapter channel 421 formed within the catheter adapter body 416 and extending between the proximal and distal ends 420, 418 of the catheter adapter body 416. In some embodiments, the catheter adapter body 416 may include a septum 470 which may be coupled to the catheter adapter body 416 adjacent the catheter adapter channel 421. In some embodiments, the septum 470 may be a single component septum. In some embodiments, the septum 470 may be a multi-component septum. In some embodiments, the catheter adapter body 416 may include an access port 480, which may be in fluid communication with the catheter adapter channel 421.

The catheter 422 may include a proximal end 426, a distal end 424, and a catheter lumen 427 extending between the proximal and distal ends 426, 424 of the catheter 422. In some embodiments, the catheter 422 may include a peripheral intravenous catheter ("PIVC"). In some embodiments, the proximal end 426 of the catheter 422 may be coupled to and/or secured within the catheter adapter body 416, such that the catheter lumen 427 may be in fluid communication with the catheter adapter channel 421 that is formed within the catheter adapter body 416.

In the embodiment shown in FIGS. 4A and 4B, a first longitudinal axis 451 of the catheter adapter channel 421 may not be coaxial with a second longitudinal axis 452 of the catheter adapter body 416. In some embodiments, at least a portion of the catheter lumen 427 proximate the catheter adapter body 416 may be coaxial with the catheter adapter channel 421 formed within the catheter adapter body 416. In some embodiments, the second longitudinal axis 452 of the catheter adapter body 416 may extend between the proximal and distal ends 420, 418 of the catheter adapter body 416 along a primary longitudinal direction of the catheter adapter body 416. In some embodiments, the second longitudinal axis 452 may be substantially parallel to the inferior surface 440 of the catheter adapter body 416. In some embodiments, the second longitudinal axis 452 may be substantially parallel to the patient's skin 1 and/or substantially parallel to a surface area of the patient's skin 1 that abuts the inferior surface 440 of the catheter adapter body 416.

In some embodiments, the first longitudinal axis 451 of the catheter 422 and/or the catheter adapter channel 421 may form an angle 460 with respect to the second longitudinal axis 452 of the catheter adapter body 416, as illustrated in FIG. 4B.

In some embodiments, the angle 460 formed between the first longitudinal axis 451 of the catheter 422 or catheter adapter channel 421 and the second longitudinal axis 452 of the catheter adapter, the inferior surface 440 of the catheter adapter body 416, and/or the surface area of the patient's skin that abuts the inferior surface 440 of the catheter adapter body 416, may be greater than 4 degrees.

In some embodiments, the angle 460 formed between the first longitudinal axis 451 of the catheter 422 or catheter adapter channel 421 and the second longitudinal axis 452 of the catheter adapter, the inferior surface 440 of the catheter adapter body 416, and/or the surface area of the patient's skin that abuts the inferior surface 440 of the catheter adapter body 416, may be greater than 10 degrees.

In some embodiments, the angle 460 formed between the first longitudinal axis 451 of the catheter 422 or catheter adapter channel 421 and the second longitudinal axis 452 of the catheter adapter, the inferior surface 440 of the catheter adapter body 416, and/or the surface area of the patient's skin that abuts the inferior surface 440 of the catheter adapter body 416, may be greater than 4 degrees may be between 10 degrees and 90 degrees.

In some embodiments, the angle 460 formed between the first longitudinal axis 451 of the catheter 422 or catheter adapter channel 421 and the second longitudinal axis 452 of the catheter adapter, the inferior surface 440 of the catheter adapter body 416, and/or the surface area of the patient's skin that abuts the inferior surface 440 of the catheter adapter body 416, may be 30 degrees.

Figure 5:
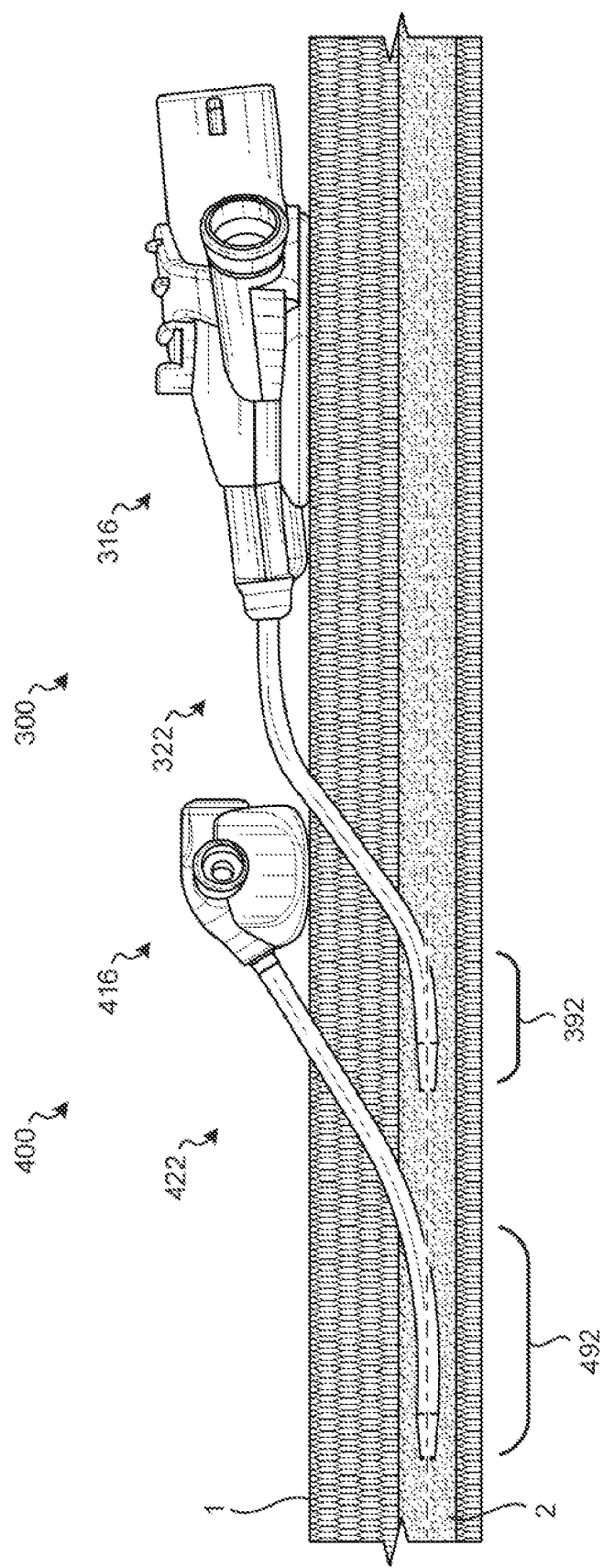
FIG. 5 is a side view of the catheter assemblies 300, 400 of FIGS. 3A and 4A inserted into the blood vessel 2 of the patient to compare relative "in-vein" lengths between the catheters 322, 422.
Figure 6:
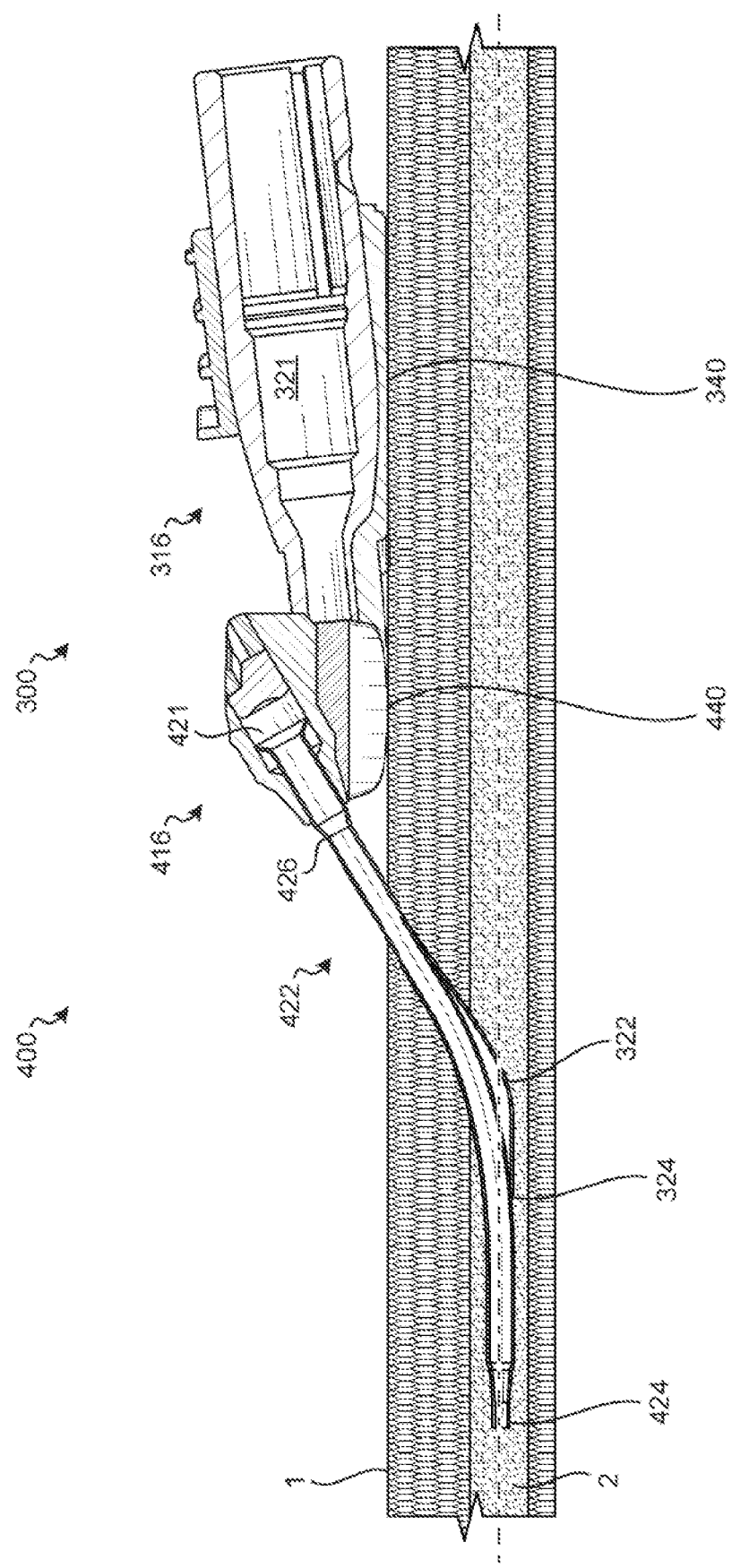
FIG. 6 is a cross-sectional side view of the catheter assemblies 300, 400 of FIGS. 3A and 4A inserted into the blood vessel 2 of the patient with the catheter assemblies 300, 400 overlaid on top of each other to compare relative "in-vein" lengths between the catheters 322, 422.

Accordingly, because the angle 460 corresponding to the catheter 422 of FIGS. 4A and 4B is relatively large (e.g., greater than 10 degrees) vs. the angles 260, 360 of the catheters 222, 322 of FIGS. 2-3B, the catheter 422 may not exhibit a substantial "S" shape in comparison to the catheters 222, 322 shown in FIGS. 2-3B. This can be seen in FIGS. 5 and 6, which compare the catheter assemblies 300, 400 to each other. Specifically, FIG. 5 is a side view of the catheter assemblies 300, 400 of FIGS. 3A and 4A inserted into the blood vessel 2 of the patient in order to compare relative in-vein lengths 392, 492 between the catheters 322, 422; and FIG. 6 is a cross-sectional side view of the catheter assemblies 300, 400 of FIGS. 3A and 4A inserted into the blood vessel 2 of the patient (with the catheter assemblies 300, 400 overlaid on top of each other) in order to compare relative in-vein lengths between the catheters 322, 422. In some embodiments, the in-vein length 492 may be 4 mm to 8 mm longer (and/or longer than 8 mm) than the in-vein length 392.

Figure 7:
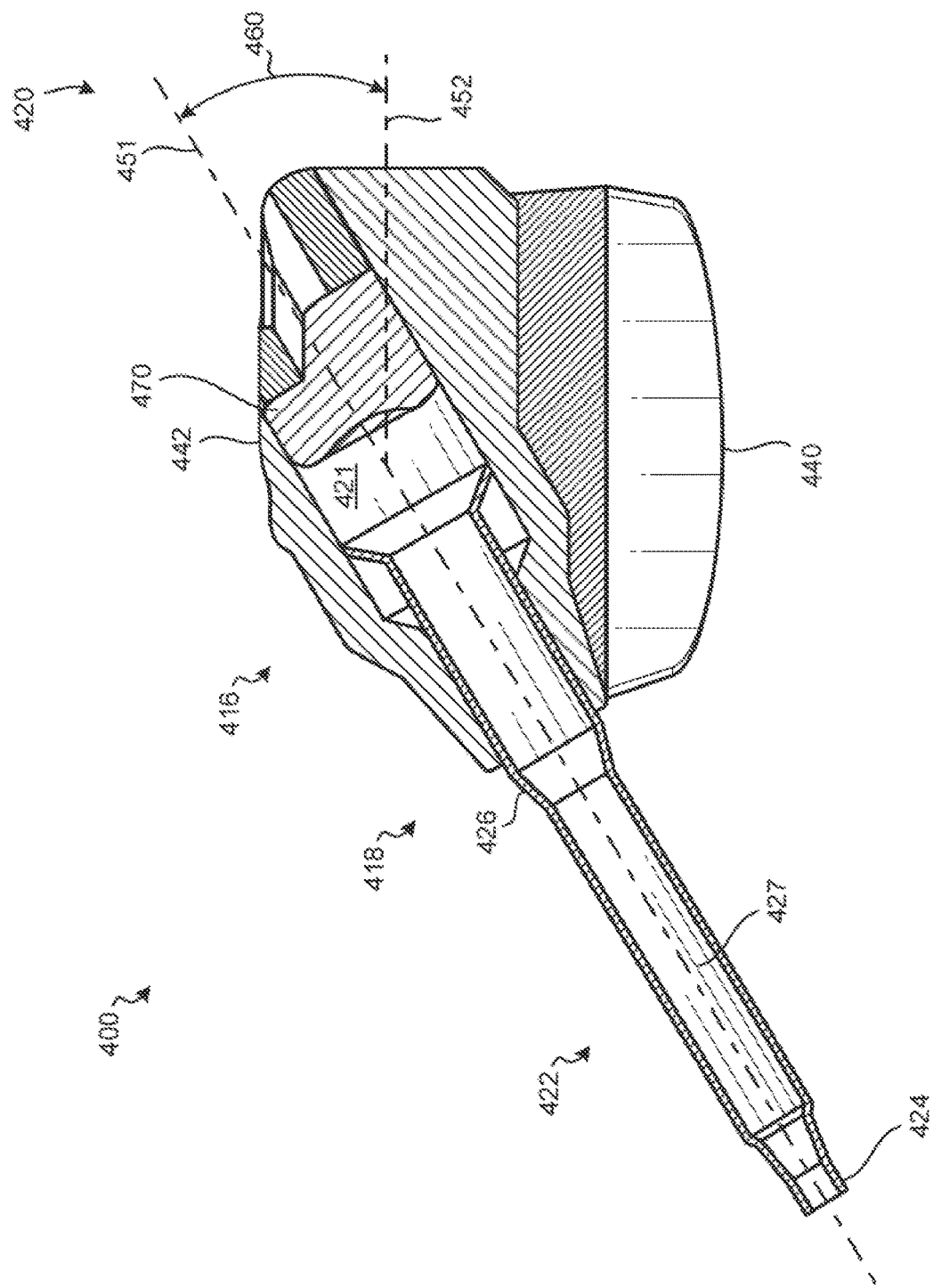
FIG. 7 is a cross-sectional side view of the catheter assembly 400 of FIG. 4A before the catheter assembly 400 is attached to a patient, according to some embodiments.
Figure 8:
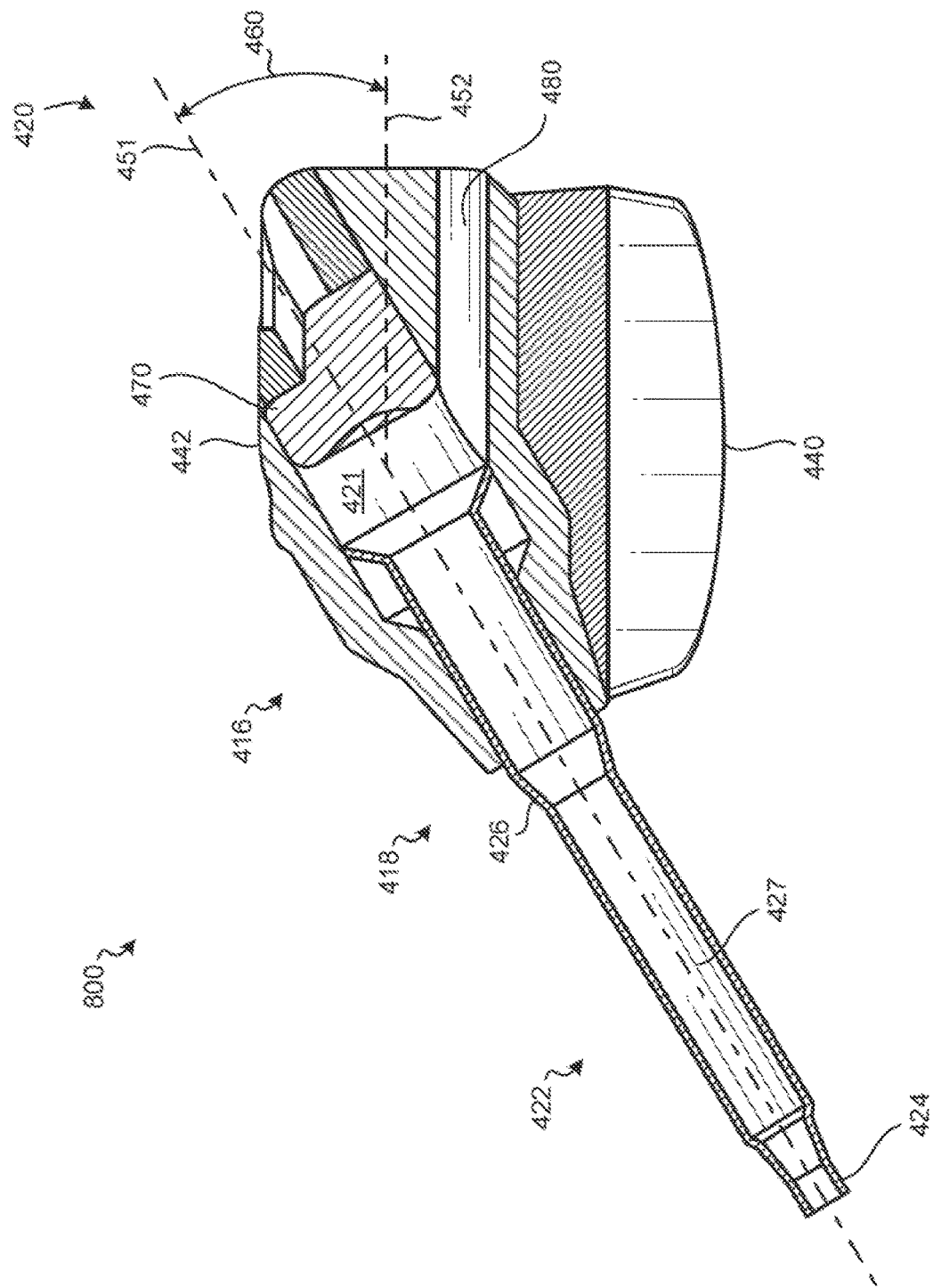
FIG. 8 is a cross-sectional side view of a catheter assembly 800 that is similar to the catheter assembly 400 of FIG. 4A including an access port 480, according to some embodiments.

FIG. 7 is a cross-sectional side view of the catheter assembly 400 of FIG. 4A before the catheter assembly 400 is attached to a patient and FIG. 8 is a cross-sectional side view of a catheter assembly 800 that is similar to the catheter assembly 400 of FIG. 4A, but which includes an access port 480, according to some embodiments.

Figure 9:
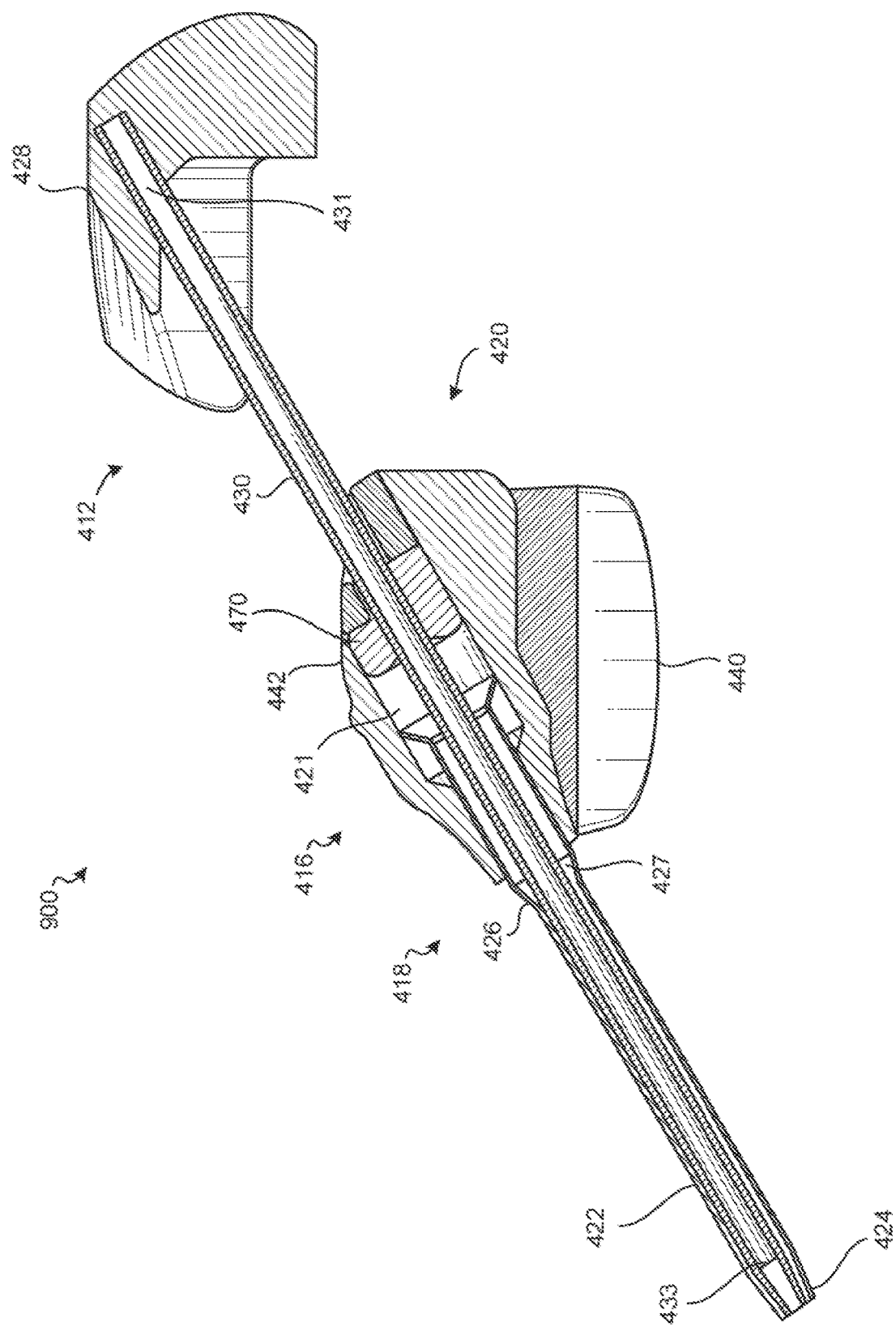
FIG. 9 is a cross-sectional side view of an example catheter system 900 that includes the catheter assembly 400 of FIG. 4A and a needle assembly 412, according to some embodiments.

FIG. 9 is a cross-sectional side view of an example catheter system 900 including the catheter assembly 400 of FIG. 4A in combination with a needle assembly 412, according to some embodiments. In some embodiments, the needle assembly 412 may include a needle hub 428 having a compact design which may be removably couplable with the catheter adapter body 416. In some embodiments, the needle assembly 412 may include an introducer needle 430 coupled to the needle hub 428. In some embodiments, a proximal end 431 of the introducer needle 430 may be secured within the needle hub 428. In some embodiments, the needle hub 428 may include a flash chamber. In some embodiments, the introducer needle 430 may extend through the catheter lumen 427 and a distal end 433 of the introducer needle 430 may protrude from the distal end 424 of the catheter 422 when the catheter system 900 is in an insertion position, ready for insertion into a vein of a patient (not shown in FIG. 9). In some embodiments, the introducer needle 430 may be removably insertable within the catheter adapter channel 421 and the catheter lumen 427. In some embodiments, the introducer needle 430 may be removed from the catheter adapter channel 421 and/or the catheter lumen 427 at an angle with respect to the patient's skin 1, the inferior surface 440 of the catheter adapter body 416, and/or the second longitudinal axis 452 of the catheter adapter body 416, that is greater than 10 degrees. In some embodiments, the introducer needle 430 may be removed from the catheter adapter channel 421 and/or the catheter lumen 427 at an angle with respect to the patient's skin 1, the inferior surface 440 of the catheter adapter body 416, and/or the second longitudinal axis 452 of the catheter adapter body 416, that is 30 degrees.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions.

A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or −10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A catheter assembly comprising:
   a catheter adapter body, the catheter adapter body comprising:
   a proximal end;
   a distal end;
   an inferior surface;
   a superior surface, wherein the superior surface comprises an uppermost surface of the catheter assembly and is fixed with respect to the inferior surface, the distal end of the catheter adapter body and the proximal end of the catheter adapter body extending between the superior surface and the inferior surface; and
   a catheter adapter channel formed within the catheter adapter body and having a linear axis extending from the superior surface through the distal end of the catheter adapter body; and
   a catheter comprising:
   a proximal end;
   a distal end; and
   a catheter lumen extending between the proximal end and the distal end of the catheter,
   wherein:
   the proximal end of the catheter is coupled to the catheter adapter body such that the catheter lumen is in fluid communication with the catheter adapter channel and
   an angle formed between the inferior surface of the catheter adapter body and a first longitudinal axis of the catheter adapter channel is greater than 4 degrees.

2. The catheter assembly of claim 1, wherein:
the catheter adapter body comprises a second longitudinal axis extending between the proximal and distal ends of the catheter adapter body; and
an angle formed between the first and second longitudinal axes is greater than 10 degrees.

3. The catheter assembly of claim 2, wherein the angle formed between the first and second longitudinal axes is between 10 degrees and 90 degrees.

4. The catheter assembly of claim 3, wherein the angle formed between the first and second longitudinal axes is 30 degrees.

5. The catheter assembly of claim 1, wherein at least a portion of the catheter lumen proximate the catheter adapter body is coaxial with the catheter adapter channel formed within the catheter adapter body.

6. The catheter assembly of claim 1, further comprising a septum coupled to the catheter adapter body adjacent the catheter adapter channel, wherein the septum comprises one of:
   a single component septum; and
   a multi-component septum.

7. The catheter assembly of claim 1, wherein the catheter adapter body further comprises an access port in fluid communication with the catheter adapter channel.

* * * * *